United States Patent
Kim et al.

(10) Patent No.: US 11,266,509 B2
(45) Date of Patent: Mar. 8, 2022

(54) ANATOMICALLY SHAPED KNEE JOINT AUGMENT

(71) Applicant: CORENTEC CO., LTD., Chungcheongnam-do (KR)

(72) Inventors: Chan-Eol Kim, Seoul (KR); Sang-Gil Lee, Hanam-si (KR); Young-Woong Jang, Seoul (KR); Oui-Sik Yoo, Seoul (KR); Seok-Joo Kim, Seoul (KR)

(73) Assignee: Corentec Co., Ltd., Chungcheongnam-do (KR)

( * ) Notice: Subject to any disclaimer, the term of this patent is extended or adjusted under 35 U.S.C. 154(b) by 55 days.

(21) Appl. No.: 16/765,764

(22) PCT Filed: Nov. 15, 2018

(86) PCT No.: PCT/KR2018/013955
§ 371 (c)(1),
(2) Date: May 20, 2020

(87) PCT Pub. No.: WO2019/107805
PCT Pub. Date: Jun. 6, 2019

(65) Prior Publication Data
US 2020/0281731 A1    Sep. 10, 2020

(30) Foreign Application Priority Data
Nov. 30, 2017    (KR) .......................... 10-2017-0162578

(51) Int. Cl.
*A61F 2/38* (2006.01)
*A61F 2/30* (2006.01)

(52) U.S. Cl.
CPC .......... *A61F 2/389* (2013.01); *A61F 2/30734* (2013.01); *A61F 2002/30736* (2013.01)

(58) Field of Classification Search
CPC .................. A61F 2/389; A61F 2/30734; A61F 2002/30736
See application file for complete search history.

(56) References Cited

U.S. PATENT DOCUMENTS 8,771,364 B2    7/2014    May et al.
2014/0222155 A1*  8/2014    Metzger .............. A61F 2/30734
                                        623/20.15
(Continued)

FOREIGN PATENT DOCUMENTS

JP    2990521 B2    12/1999
JP    2012-505726 A    3/2012
(Continued)

OTHER PUBLICATIONS

International Search Report dated May 7, 2019, issued in PCT Application No. PCT/KR2018/013955, filed Nov. 15, 2018.
(Continued)

*Primary Examiner* — Javier G Blanco
(74) *Attorney, Agent, or Firm* — Workman Nydegger (57) ABSTRACT

The present disclosure relates to a knee joint augment having an anatomical shape. More specifically, the present disclosure relates to a knee joint augment that is used for artificial joint replacement to replace lost bone, wherein the augment is used in artificial knee replacement surgery to be coupled to a knee implant. The augment includes a top surface configured to be brought into contact with a distal surface of a base plate that forms the body of a tibia element and a bottom surface configured to be brought into contact with a cut surface of a tibia. The bottom surface has an area smaller than that of the top surface, and has a tapered shape that narrows from the top to the bottom. An intermediate line at which one end surface cut to be perpendicular to the top surface and an outer surface meet each other has a shape that is outwardly convex to the outside of the augment with (Continued)

respect to a straight line connecting a top point where the intermediate line and the top surface meet and a bottom point where the intermediate line meets the bottom surface, whereby the intermediate line has a shape corresponding to the anatomical shape of a cut bone.

7 Claims, 9 Drawing Sheets

(56) References Cited

U.S. PATENT DOCUMENTS

| | | | | |
|---|---|---|---|---|
| 2014/0277528 A1* | 9/2014 | Mines | ................. | A61F 2/30734 623/20.16 |
| 2014/0277539 A1* | 9/2014 | Cook | ................. | A61F 2/30734 623/20.32 |
| 2015/0335438 A1* | 11/2015 | Pierce | ....................... | A61F 2/38 623/20.32 |

FOREIGN PATENT DOCUMENTS

| | | | |
|---|---|---|---|
| JP | 2014-176686 A | 9/2014 | |
| JP | 2016-506817 A | 3/2016 | |
| KR | 10-1872791 B1 | 6/2018 | |
| WO | WO-9730661 A1 * | 8/1997 | ......... A61B 17/1668 |

OTHER PUBLICATIONS

Written Opinion dated May 7, 2019, issued in PCT Application No. PCT/KR2018/013955, filed Nov. 15, 2018.

* cited by examiner

FIG. 17

ANATOMICALLY SHAPED KNEE JOINT AUGMENT

BACKGROUND OF THE INVENTION

1. The Field of the Invention

The present disclosure relates to a knee joint augment having an anatomical shape. More specifically, the present disclosure relates to a knee joint augment that is used for artificial joint replacement to replace lost bone, wherein the augment is used in artificial knee replacement surgery to be coupled to a knee implant. The augment includes a top surface configured to be brought into contact with a distal surface of a base plate that forms the body of a tibia element and a bottom surface configured to be brought into contact with a cut surface of a tibia. The bottom surface has an area smaller than that of the top surface, and has a tapered shape that narrows from the top to the bottom. An intermediate line at which one end surface cut to be perpendicular to the top surface and an outer surface meet each other has a shape that is outwardly convex to the outside of the augment with respect to a straight line connecting a top point where the intermediate line and the top surface meet and a bottom point where the intermediate line meets the bottom surface, whereby the intermediate line has a shape corresponding to the anatomical shape of a cut bone.

2. Description of the Prior Art

A knee joint is a joint part that interconnects a tibia and a femur. When a joint loses its function due to abrasion, external injury, or the like, a knee replacement procedure is performed to install an implant capable of replacing the joint.

Figure 1:
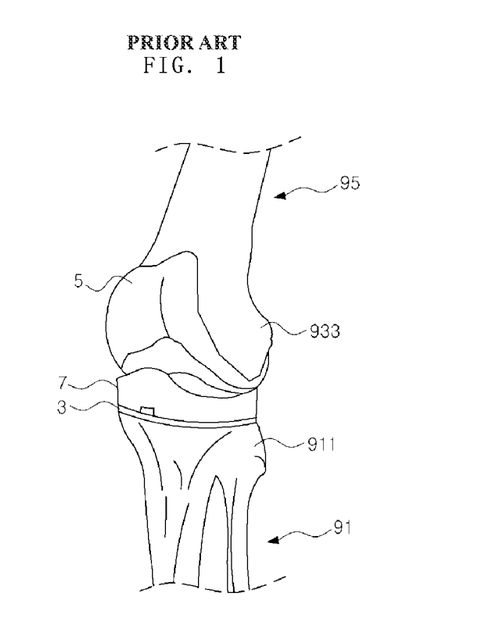
FIG. 1 is a perspective view illustrating the state in which a knee implant is implanted.

Referring to FIG. 1, it can be seen that an implant is inserted between a femur 93 located above the knee and a tibia 91 located below the knee. This knee joint implant includes: a femur element 5, which is implanted in a distal portion 933 of the femur 93 after partially cutting the distal portion 933 of the femur 93; a tibia element 3, which is implanted in a proximal portion 911 of the tibia 91 after partially cutting the proximal portion 911 of the tibia 91; and an insert 7 configured to serve as a bearing between the femur element 5 and the tibia element 3. In the case of revision or the like, the proximal portion 911 of the tibia 91 is cut in a considerable amount, and thus only the thin tibia element 3 cannot replace all of the cut portions. Accordingly, a separate member to replace the bones in the cut portions is required.

Figure 2:
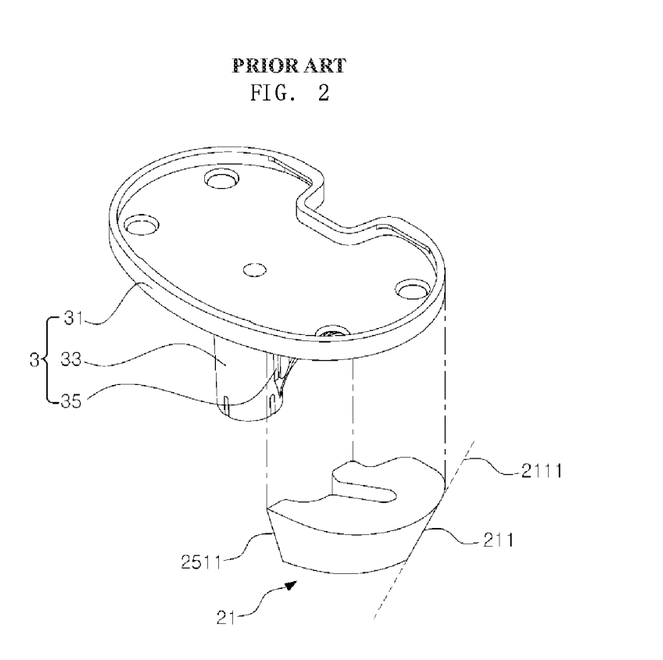
FIG. 2 is an exploded perspective view illustrating a process in which an augment according to the prior art is coupled to a tibia element.

Referring to FIG. 2, it can be seen that an augment 21 is used for replacing the proximal portion 911 of the tibia 91 thus cut. The augment 21 is in contact with the bottom surface of the base plate 31 constituting the upper portion of the tibia element 3, and is coupled to the side surfaces of a stem 33 and a wing 35, which extend downward from the base plate 31 by a predetermined length. In this state, the augment is coupled to the proximal portion 911 of the tibia 91 so as to bear the load on behalf of the cut bone.

However, the conventional augment 21 has a problem in that a line 211 connecting the top surface and the bottom surface of the augment 21 on the side surface has the shape of a straight line 2111 and does not conform to the shape of the tibia 91 of the cut area. This can be seen more clearly in FIG. 3.

Figure 3:
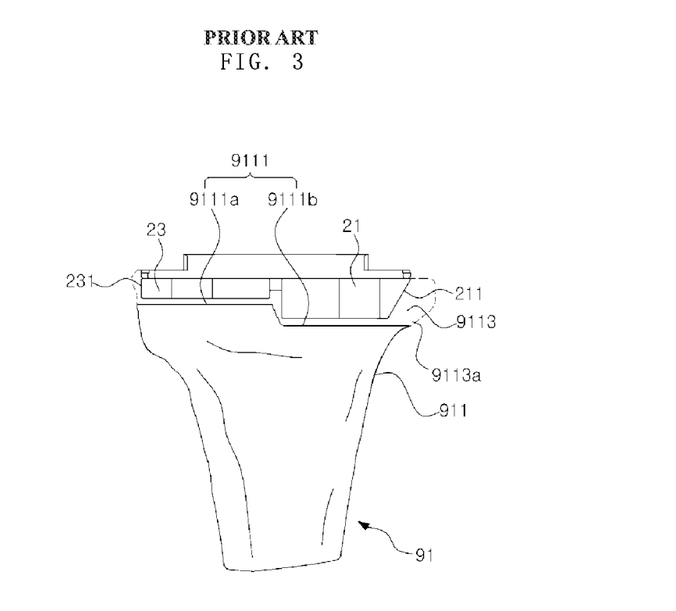
FIG. 3 is a front view illustrating the state in which an augment and a tibia element according to the prior art are coupled to a proximal portion of a tibia element.

Referring to FIG. 3, it can be seen that a portion of the proximal portion 911 of the tibia 91 is cut and forms a cut surface 9111 of the tibia 91. In some cases, two cut surfaces 9111a and 9111b having different heights may be formed, and augments 21 and 23 are positioned on the cut surfaces 9111a and 9111b, respectively. However, the side surface 211 of the augment 21 extends in a straight line shape from the bottom to the top. Since the proximal portion 911 of the actual tibia 91 widens upwards, but is bent so that its slope becomes gradually steeper, the conventional augment 21 having the side surface in the straight line shape has a problem in that it does not conform to the actual patient's bone shape. The augment 23 having a slightly different shape also has this problem. When the shape of the augment 21 or 23 is different from the actual bone shape, it is impossible for the augment 21 or 23 to appropriately replace lost bone 9113.

The disclosure disclosed in Korean Registration Patent No. 10-1744737 (Registration Date: Jun. 1, 2017) relates to an augment capable of replacing a cut portion of a tibia in a knee implant.

However, in the above-mentioned disclosure, the shape of the side surface also does not properly simulate the shape of the cut proximal portion 911 of a tibia 91 as in the prior art described above.

When the augment 21 or 23 having a shape different from the bone shape of the cut portion is used, the patient may be unable to properly tolerate pain caused by a load applied from the upper side even after recovering from surgery and returning to daily life. That is, the load applied when the recovered patient performs an action such as standing and walking is distributed differently from the load distributed to the bone that existed before. Due to this abnormal load distribution, the life of the implant may be shortened, or an excessive load may be applied only to one side of the cut surface 9111.

Furthermore, since the augments 21 and 23 in the prior art do not properly implement the shape of a cut bone, an implant may protrude to the outside of the cut surface 9111.

Figure 4:
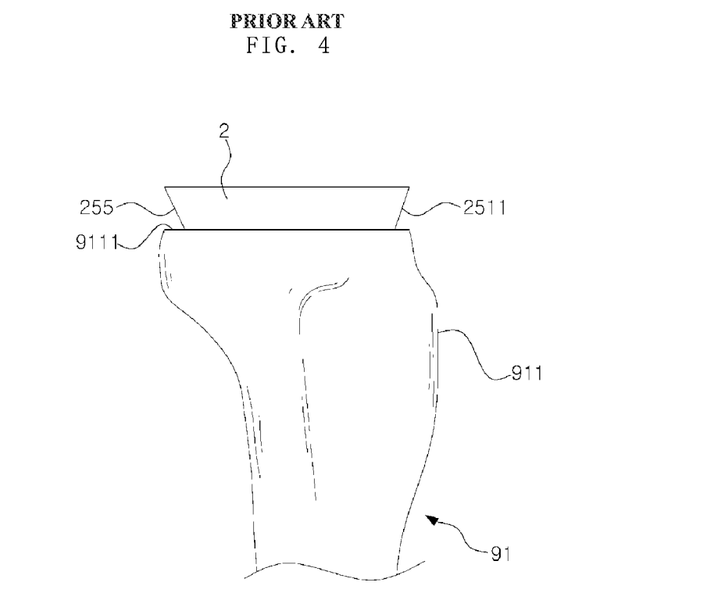
FIG. 4 is a side view illustrating the state in which the augment according to the prior art is implanted into the tibia element and the alignment state thereof is checked while looking from a lateral side.

Meanwhile, as can be seen from FIG. 2, in the conventional augments 21 and 23, a front boundary line, which is a boundary where the inner side surface and the outer side surface meet on the front side, extends forming an acute angle with the top surface. When an angle other than 90 degrees, there is a disadvantage in that it is not easy to check the alignment state between the tibia and the reinforcing members 21 and 23 with a naked eye when checking the implantation state from the side through an X-ray image or the like after the procedure. This also applies to the rear surface 255 (see FIG. 4). The prior art is also illustrated in FIG. 4. When a misalignment state is erroneously determined as described above, many problems are caused. For example, the patient's health is adversely affected in the long term.

In addition, the conventional reinforcing members 21 and 23 are combined one by one on both sides of the tibia element, wherein the shapes of the augments 21 and 23 on both sides are not symmetrical but have different shapes. Thus, augments made for use on a right knee could not be used on a left knee, and vice versa. Since the shapes of the augments on the both sides are different, a total of four augments having different shapes are required for the inside and outside of the right knee and the inside and outside of the left knee, which causes inefficiency in production.

Accordingly, there are needs for augments that are capable of realizing a normal load distribution through a shape that conforms to a bone shape of a cut portion, capable of reinforcing lost bone as much as possible, capable of allowing the alignment state after the procedure to be easily checked, and capable of being used in both knees with only two types of augments.

SUMMARY OF THE INVENTION

The present disclosure has been conceived in order to solve the problems described above.

An object of the present disclosure is to provide a knee joint augment having an anatomical shape of a structure that allows lost bone to be reinforced as much as possible through the augment having the shape conforming to the anatomical shape of a tibia.

Another object of the present disclosure is to provide a knee joint augment having an anatomical shape capable of implementing a normal load distribution during excise of the patient recovered after surgery by forming the outer surface of the augment as a curved surface so as to configure the augment to have a shape that conforms to the shape of the lost proximal portion of a tibia as much as possible.

Still another object of the present disclosure is to provide a knee joint augment having an anatomical shape of a structure capable of preventing an implant or bone from being damaged by implementing a normal load distribution through an augment having an anatomical shape such that force is prevented from concentrating on only one side.

Still another object of the present disclosure is to provide a knee joint augment having an anatomical shape capable of preventing an implant from protruding when replacing lost bone using an augment including an outer surface formed as a curved surface.

Still another object of the present disclosure is to provide a knee joint augment having an anatomical shape capable of increasing the life of an implant by preventing damage of the implant or bone through a normal load distribution.

Still another object of the present disclosure is to provide a knee joint augment having an anatomical shape of a structure capable of withstanding a load applied to the knee through a smooth load distribution even when the load is applied in the state in which the axis of the knee is distorted while the patient who recovered after surgery is exercising.

Still another object of the present disclosure is to provide a knee joint augment having an anatomical shape of a structure capable of facilitating an alignment checking operation by making it possible to quickly and accurately check the alignment state when checking the alignment state of an augment through an X-ray photo taken from a lateral side after the surgery is completed, and capable of increasing the life of an implant.

Yet another object of the present disclosure is to provide a knee joint augment having an anatomical shape, in which two augments to be coupled to opposite sides of a tibia element are made to be symmetrical to each other such that the augments can be used for both of left and right knees with only two types of augments, whereby the knee joint augment can be conveniently manufactured.

In order to achieve the objects of the present disclosure, the present disclosure is implemented by embodiments configured as follows.

According to an embodiment of the present disclosure, there is provided an augment used in artificial joint replacement so as to replace lost bone, wherein the augment has a shape corresponding to an anatomical structure of the lost bone.

According to an embodiment of the present disclosure, the augment is used in artificial knee replacement surgery to be coupled to a knee joint implant, and includes a top surface configured to come into contact with a distal surface of a base plate forming a body of a tibia element and a bottom surface configured to come into contact with a cut surface of the tibia.

According to an embodiment of the present disclosure, the bottom surface of the augment has a shape having a smaller area than the top surface so as to correspond to the anatomical structure of the lost tibia.

According to an embodiment of the present disclosure, an outer surface connecting the top and bottom surfaces of the augment is formed as a curved surface so as to correspond to the anatomical structure of the lost tibia.

According to an embodiment of the present disclosure, the outer surface of the augment is formed as a curved surface that is continuously inwardly inclined from the top surface toward the bottom surface.

According to an embodiment of the present disclosure, the outer surface of the augment is formed as a curved surface that is outwardly convex while extending from the top surface to the bottom surface.

According to an embodiment of the present disclosure, a middle line at which one end surface cut to be perpendicular to the top surface meets the outer surface has a curved shape that is outwardly convex.

According to an embodiment of the present disclosure, a middle line at which one end surface cut to be perpendicular to the top surface meets the outer surface takes a form of a curved line convex to the outside of the augment with respect to a straight line connecting a top point at which the middle line meets the top surface and a bottom point at which the middle line meets the bottom surface.

According to an embodiment of the present disclosure, the inner surface connecting the top surface and the bottom surface of the augment extends to be perpendicular to the top surface.

According to an embodiment of the present disclosure, the anterior boundary line at which the outer surface and the inner surface meet at the anterior side extends to be perpendicular to the top surface.

According to an embodiment of the present disclosure, the augment further includes a rear surface connecting the outer surface and the inner surface at the posterior side, and the rear surface extends to be perpendicular to the upper surface.

According to an embodiment of the present disclosure, the inner surface includes a wing accommodation surface configured to accommodate a wing of the tibia element.

According to an embodiment of the present disclosure, the inner surface includes a step accommodation surface configured to accommodate a stem of the tibia element.

According to an embodiment of the present disclosure, the top surface includes an upper recessed surface that is recessed downward by a predetermined depth in order to accommodate adhesive.

According to an embodiment of the present disclosure, the bottom surface includes a lower recessed surface that is recessed upward by a predetermined depth in order to accommodate adhesive.

According to an embodiment of the present disclosure, the augment includes a coupling hole recessed downward by a predetermined depth from the top surface of the tibia element so as to accommodate a coupling means that couples the augment to the tibia element.

According to an embodiment of the present disclosure, two augments are provided to be respectively coupled to opposite sides of the tibia element, and the two augments are formed in symmetrical shapes with reference to the stem of the tibia element, whereby the two augments can be used for both of left and right knees.

The present disclosure is capable of obtaining the following effects through a combination of the above-described embodiments and the configurations to be described below and a use relationship therebetween.

The present disclosure makes it possible to reinforce lost bone as much as possible through the augment having the shape conforming to the anatomical shape of a tibia.

The present disclosure is capable of implementing a normal load distribution during excise of the patient recovered after surgery by forming the outer surface of the augment as a curved surface so as to configure the augment to have a shape that conforms to the shape of the lost proximal portion of a tibia as much as possible.

In addition, the present disclosure is capable of preventing an implant or bone from being damaged by implementing a normal load distribution through an augment having an anatomical shape such that force is prevented from concentrating on only one side.

In addition, the present disclosure is capable of preventing an implant from protruding when replacing lost bone using an augment including an outer surface formed as a curved surface.

In addition, the present disclosure is capable of increasing the life of an implant by preventing damage of the implant or bone through a normal load distribution.

In addition, the present disclosure is capable of withstanding a load applied to the knee through a smooth load distribution even when the load is applied in the state in which the axis of the knee is distorted while the patient who recovered after surgery is exercising.

Furthermore, the present disclosure is capable of facilitating an alignment checking operation by making it possible to quickly and accurately check the alignment state when checking the alignment state of an augment through an X-ray photo taken from a lateral side after the surgery is completed, and capable of increasing the life of an implant.

According to the present disclosure, since two augments to be respectively coupled to opposite sides of a tibia element are made to be symmetrical to each other such that the augments can be used for both of left and right knees with only two types of augments, the knee joint augment can be conveniently manufactured.

BRIEF DESCRIPTION OF THE DRAWINGS

The above and other aspects, features, and advantages of the present disclosure will be more apparent from the following detailed description taken in conjunction with the accompanying drawings, in which.

DETAILED DESCRIPTION OF THE PREFERRED EMBODIMENTS

Hereinafter, a knee joint augment having an anatomical shape according to the present disclosure will be described in detail with reference to the accompanying drawings. It is to be noted that the same elements in the drawings are denoted by the same reference numerals if possible. In addition, a detailed description of well-known functions or constructions will be omitted when it may make the subject matter of the present disclosure unnecessarily unclear. Unless defined otherwise, all terms used herein have the same meaning as the general meaning of the terms understood by a person ordinarily skilled in the art to which this disclosure belongs and, when the general meaning conflicts with the meaning of the terms used herein, the meaning of the terms follows the definition used in the specification.

A knee augment having an anatomical shape according to the present disclosure will be described in detail with reference to the drawings.

Referring to FIG. 1 illustrating the state in which a knee joint implant is implanted, the knee joint implant, which is located between a distal portion 933 of a femur 93 located above the knee and a proximal portion 911 of the tibia 91 positioned below the knee, may include a femur element 5, which replaces a portion of the femur, and a tibia element 3, which replaces a portion of the tibia, and an insert 7 serving as a bearing between the femur element 5 and the tibia element 3.

In this case, a augment is required since the thin tibia element 3 alone cannot replace the entire lost bone when a large amount of the proximal portion 911 of the tibia 91 located below the tibia element 3 is cut. Prior to describing the augment 1, the configuration of the tibia element 3 will be described in detail with reference to FIGS. 13 to 15.

Figure 13:
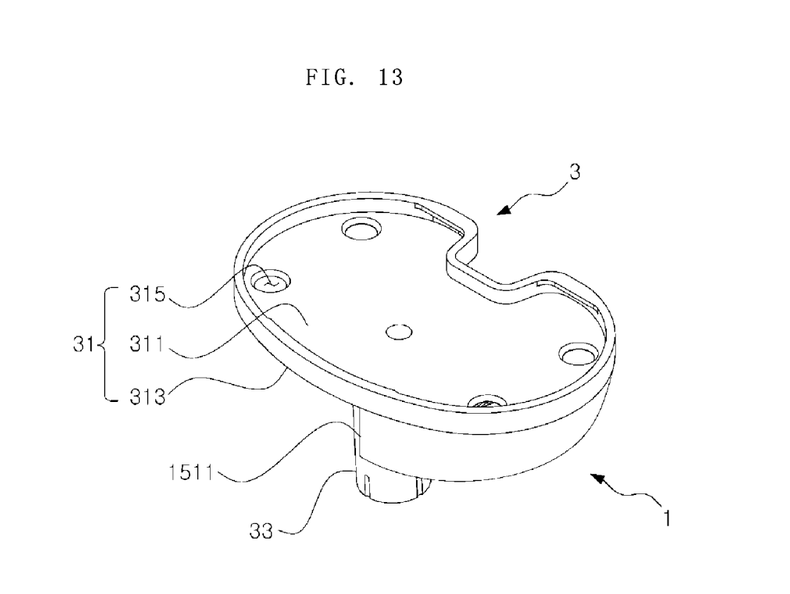
FIG. 13 is a perspective view illustrating the state in which the augment according to an embodiment of the present disclosure is coupled to a tibia element.
Figure 15:
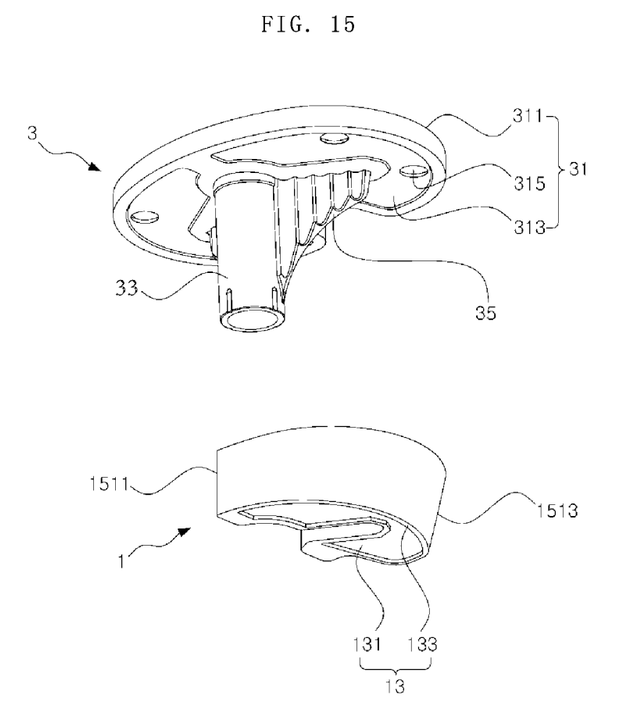
FIG. 15 is an exploded perspective view illustrating a process in which the augment according to an embodiment of the present disclosure is coupled to a tibia element.

Referring to FIGS. 13 and 15, the tibia element 3 may include a thin and wide plate-shaped base plate 31, a stem 33 extending downward from the base plate 31, and a wing 35 extending from the stem 33 and the base plate 31.

The base plate 31 is a plate having a shape corresponding to a cut tibia surface 9111 (see FIG. 16) formed in the proximal portion 911 of the tibia 91, and may include a proximal surface 311 to which the insert 7 is coupled, a cut tibia surface 9111, a distal surface 313, which is brought into contact with the cut tibia surface 9111 or the augment 1, and a coupling means accommodation hole 315 configured to accommodate a coupling means (not illustrated) to be coupled with the augment 1.

The proximal surface 311 may have a shape in which the circumference thereof protrudes upward in order to stably accommodate the insert 7 and the distal surface 313 may have a shape in which the circumference thereof protrudes upward to accommodate an adhesive or the like.

The coupling means accommodation hole 315 penetrates the base plate 31 from the proximal surface 311 to the distal surface 313. The number of coupling means accommodation holes 315 is not particularly limited. However, in the example illustrated in FIG. 14, a total of four coupling means accommodation holes are provided, two on each side.

The stem 33 extends downward by a predetermined length from the center of the distal surface 313 of the base plate 31, and is deeply embedded in the proximal portion 911 of the tibia 91 so as to provide a fixing force such that the tibia element 3 cannot be separated.

The wing 35 functions to reinforce the fixing force of the stem 33, and prevents the tibia element 3 from being rotated around the stem 33 having a cylindrical shape. The wing is no particularly limited in shape and number. In the example illustrated in FIG. 15, two wings are formed in a shape inclined rearward.

Figure 5:
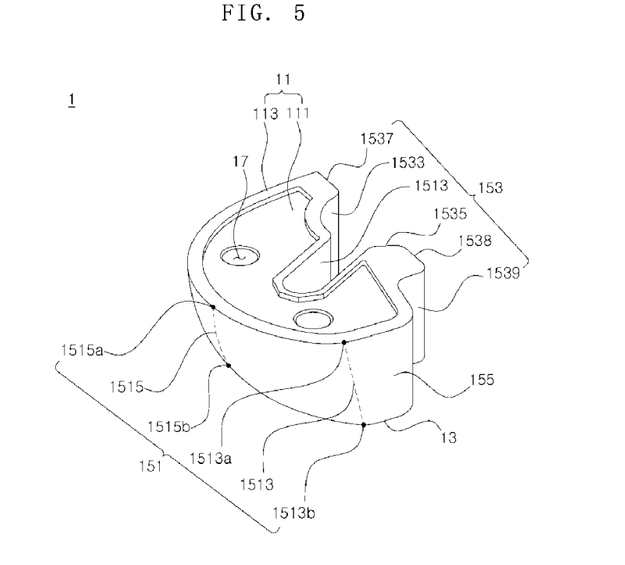
FIG. 5 is a perspective view illustrating an augment according to an embodiment of the present disclosure.

Referring to FIG. 5, the augment 1 according to the present disclosure may include a top surface 11 to come into contact with the distal surface 313 of the base plate 31, a bottom surface 13 to come into contact with the cut surface 9111 of the tibia 91, a side surface 15 connecting the top surface 11 and the bottom surface 13, and coupling holes 17 recessed downward from the top surface 11 by a predetermined depth.

Figure 6:
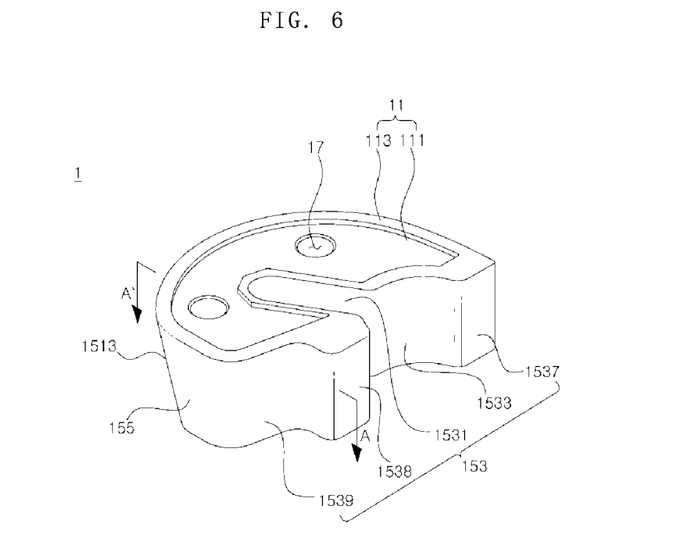
FIG. 6 is a perspective view illustrating the augment according to an embodiment of the present disclosure.
Figure 11:
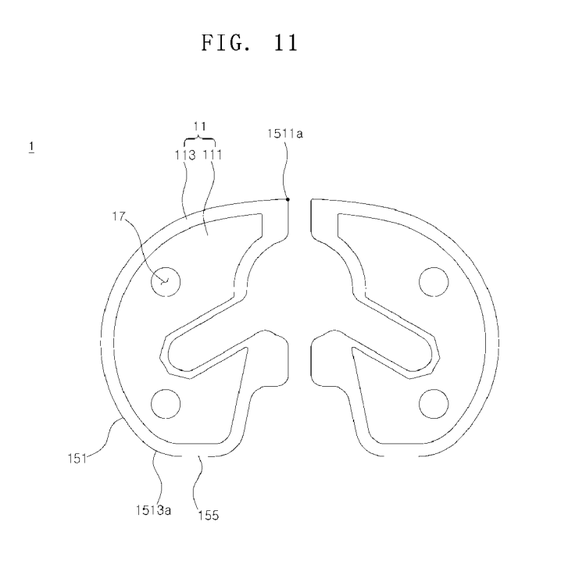
FIG. 11 is a plan view illustrating the augment according to an embodiment of the present disclosure.

Referring to FIGS. 5, 6 and 11, the top surface 11 has a shape that partially conforms to the cut surface 9111 of the tibia 91 to be in close contact with the distal surface 313 of the base plate 31 without a gap. In general, since two augments are coupled to one tibia element 3, one on each of the left and right sides thereof, each augment has a shape corresponding to a half portion of the cut tibia surface 9111. In this case, adhesive or the like is required to couple the augments to the distal surface 313. Thus, the distal surface may include an upper recessed surface 111, which is recessed by a predetermined depth in the intermediate portion in order to accommodate the adhesive or the like, and an upper boundary 113 that protrudes upward with respect to the upper recessed surface 111 by a predetermined length to form a circumference.

Figure 12:
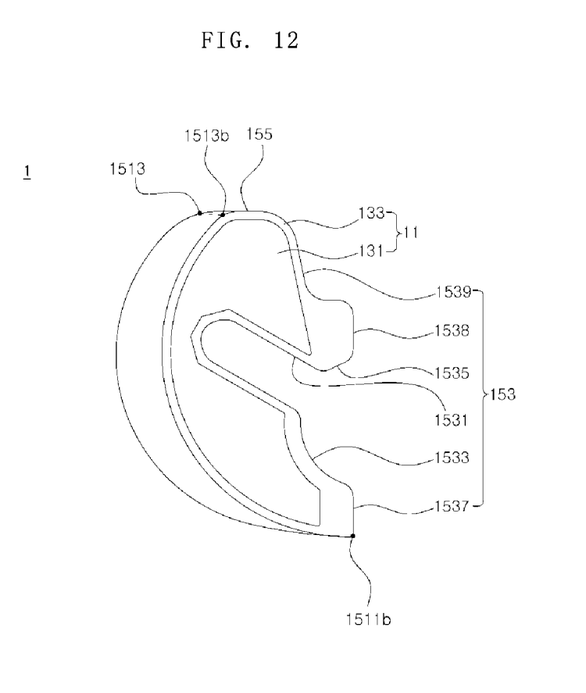
FIG. 12 is a bottom view illustrating the augment according to an embodiment of the present disclosure.

Referring to FIG. 12, the bottom surface 13 is a surface to be directly in contact with the cut surface 9111 of the tibia 91. Like the top surface 13, the bottom surface has the same shape as the cut tibia surface 9111. In general, since two augments 1 are coupled to one tibia element 3, one on each of the left and right sides thereof, each augment has a shape corresponding to a half portion of the cut tibia surface 9111. In this case, adhesive or the like is required to couple the augments to the cut tibia surface 9111. Thus, the distal surface may include a lower recessed surface 131, which is recessed by a predetermined depth in the intermediate portion in order to accommodate the adhesive or the like, and a lower boundary 133 that protrudes downward with respect to the lower recessed surface 131 by a predetermined length to form a circumference.

The side surface 15 is a surface connecting the top surface 11 and the bottom surface 13, and may include an inner surface 153 facing the stem 33 side of the tibia element 3, an outer surface 151 facing away from the stem 33, and a rear surface 155 facing the rear side.

Referring to FIGS. 5, 6, and 11, the inner surface 153 may extend to be perpendicular to the top surface 11, and may include first and second stem accommodation surfaces 1533 and 1535 configured to come into contact with the stem 33, a wing accommodation surface 1531 configured to come into contact with the wing 35, an anterior-facing surface 1537 facing the augment 1 coupled to the opposite side from the anterior, a posterior-facing surface 1538 facing the augment 1 coupled to the opposite side from the posterior, and a connection surface 1539 connecting the anterior-facing surface 1538 and the rear surface 155.

The first and second stem accommodation surfaces 1533 and 1535 are surfaces configured to come into contact with the stem 33 of the tibia element 3. When the stem 33 is a cylindrical column, each of the first and second stem accommodation surfaces 1533 and 1535 has a concavely curved surface in the inside thereof. In this case, the surface configured to come into contact with the stem 33 at the front side may be referred to as a first stem accommodation surface 1533 and the surface configured to come into contact with the stem 33 at the rear side may be referred to as a second stem accommodation surface 1535. The state in which the stem accommodation surfaces 1533 and 1535 and the stem 33 come into contact each other are illustrated in detail in FIG. 14, which will be described later.

The wing accommodation surface 1531 is a surface configured to accommodate the wing 35 of the tibia element 3, and the shape of the wing accommodation surface 1531 may be changed depending on the shape of the wing 35. As illustrated in the drawings annexed to the present specification, the wing 35 is formed in the form of a thin plate that is inclined rearward, and thus the wing accommodation surface 1531 is also biased to the rear side, and is deeply recessed inward of the augment 1 in order to accommodate the thin plate. The state in which the wing 35 is accommodated inside the wing accommodation surface 1531 is illustrated in detail in FIG. 15, which will be described later.

Figure 16:
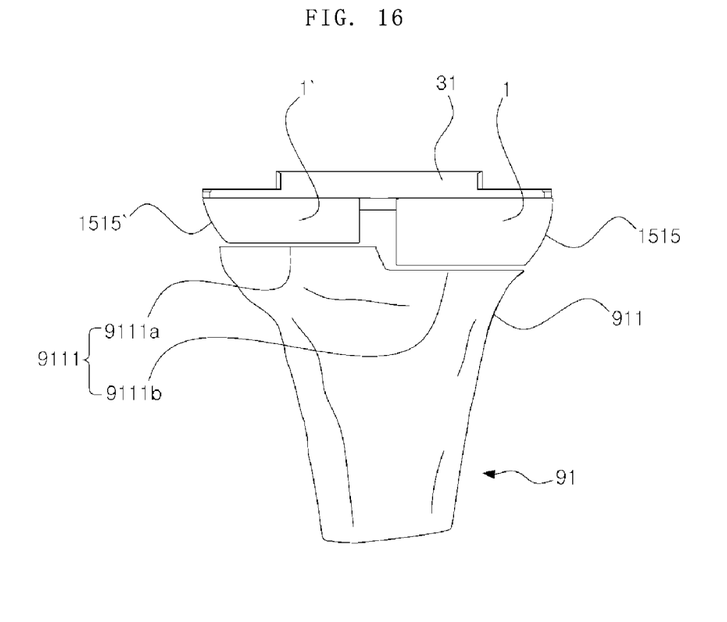
FIG. 16 is a front view illustrating the state in which the augment and the tibia element according to an embodiment of the present disclosure are coupled to a proximal portion of a tibia.

As illustrated in FIG. 16, two augments 1 may be typically coupled to one tibia element 3. The anterior-facing surface 1537 is the surface that faces the augment 1 coupled to the opposite side, and meets the outer surface 151 with reference to an anterior boundary line 1511, which will be described later.

The posterior-facing surface 1538 performs the same function as the anterior-facing surface 1537, and faces the augment 1 coupled to the opposite side as illustrated in FIG. 16.

The connection surface 1539 is a surface that connects the posterior-facing surface 1538 and the rear surface 155, and may be bent along the circumference of the base plate 31.

All of the above-described surfaces 1531 to 1539 may be connected at an acute angle in a region where they are connected to each other, but may have a blunt edge as illustrated in the drawings annexed to the present specification.

The outer surface 151 is a side surface positioned opposite the inner surface 153, and connects the anterior-facing surface 1537 and the rear surface 155 back and forth. At this time, the outer surface 151 may form a curved surface when extending back and forth along the periphery of the cut surface 9111 of the tibia 91 and the base plate 31 having a shape conforming to the cut surface 9111. This is also illustrated in FIG. 11, which is a plan view, and FIG. 12, which is a bottom view.

Figure 10:
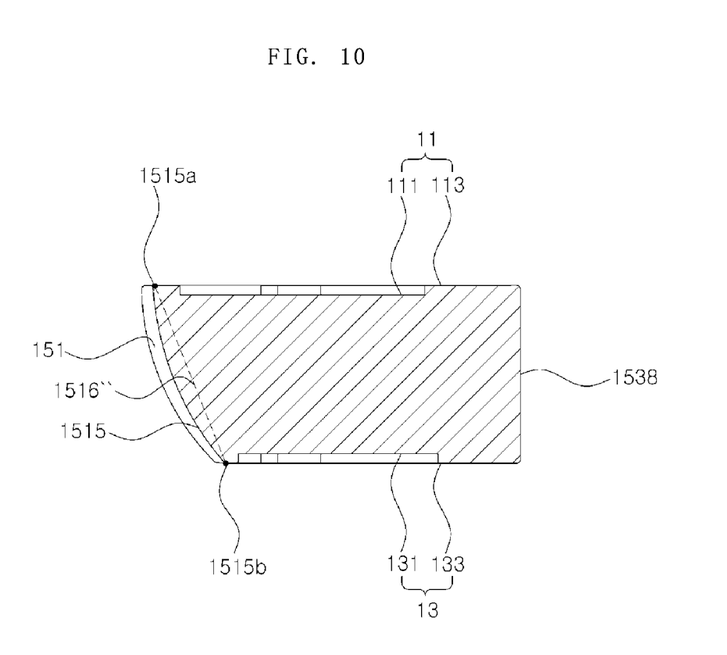
FIG. 10 is a cross-sectional view of the augment taken along line A-A' in FIG. 6.

In addition, the outer surface 151 may form a curved surface when it goes from the bottom surface 13 to the top surface 11, which will be described with reference to FIG. 7, which is a rear view, FIG. 8, which is a front view, and FIG. 10, which is a cross-sectional view.

Figure 7:
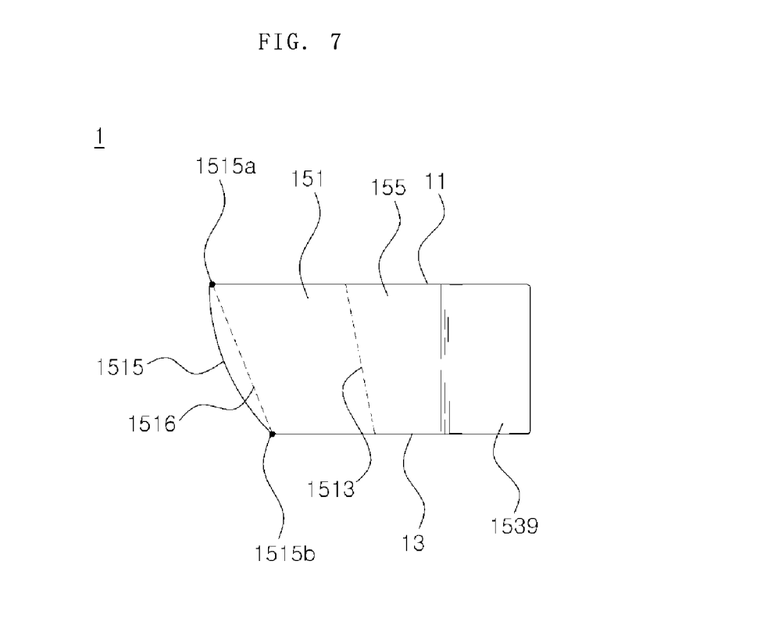
FIG. 7 is a rear view illustrating the augment according to an embodiment of the present disclosure.

Referring to FIG. 7, which is a rear view of the augment 1, among the countless curves forming the outer surface 151, a middle line 1515 connecting the top surface 11 and the bottom surface 13 at the shortest distance is shown in the drawing. At this time, the concept of the middle line 1515 does not necessarily mean one specific line, but may include a plurality of lines formed by intersection of a cross section (e.g., the cross section taken along line A-A' in FIG. 6) perpendicular to the top surface 11 and the outer surface 151. Assuming that the point where the middle line 1515 meets the top surface 11 is a top point 1515a and the point where the middle line 1515 meets the bottom surface 13 is a bottom point 1515b, the middle line 1515 takes a form of a curved line convexly protruding to the outside of the augment 1 with respect to a straight line 1516 that connects the top point 1515a and the bottom point 1515b.

Figure 8:
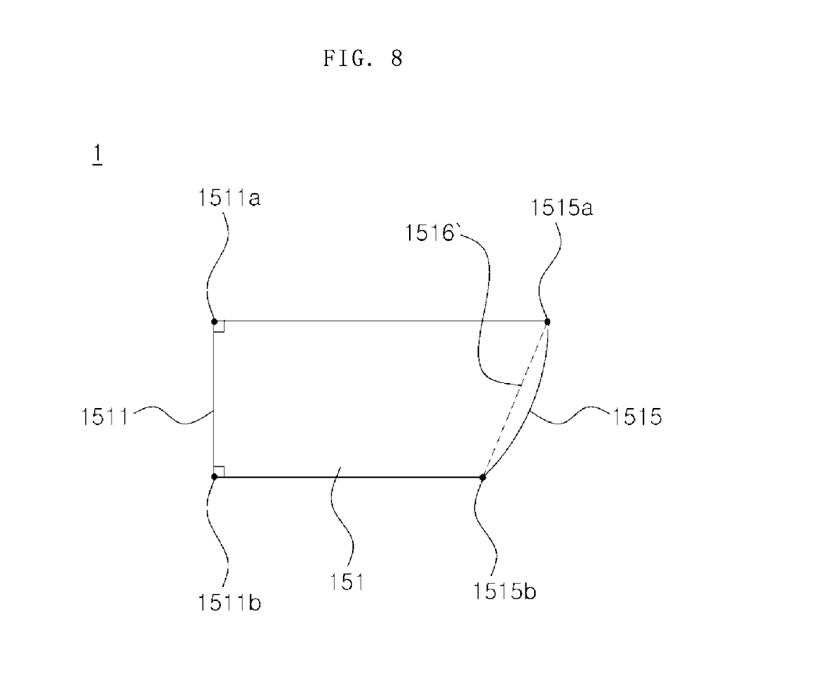
FIG. 8 is a front view illustrating the augment according to an embodiment of the present disclosure.

This can be seen in FIG. 8, which is a front view of the augment 1. The middle line 1515 has a curved line shape convexly protruding to the outside of the augment 1 with respect to a straight line 1516' that straightly connects the top point 1515a and the bottom point 1515b.

Figure 9:
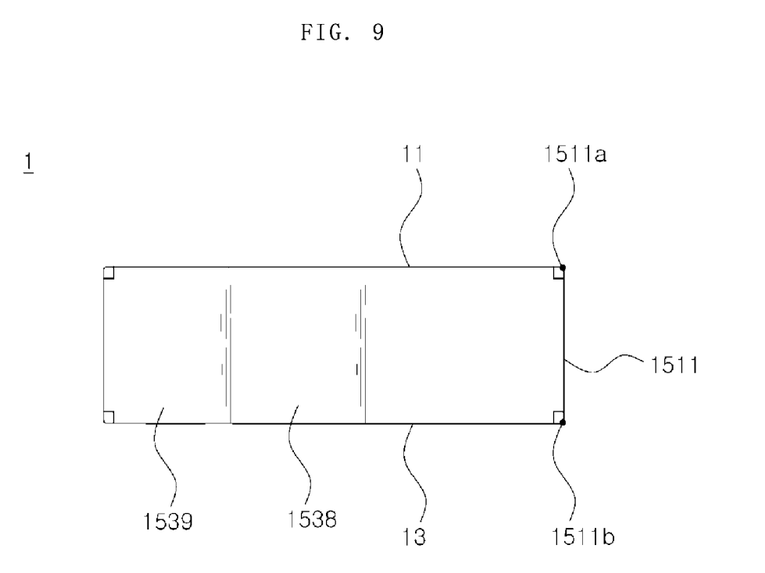
FIG. 9 is a side view illustrating the augment according to an embodiment of the present disclosure.

Referring to FIG. 9 obtained by viewing the cross section taken along the line A-A' of FIG. 6, it can be seen that another middle line 1515 also convexly protrudes to the outside of a straight line 1516" that straightly connects the top point 1515a and the bottom point 1515b.

In this way, the outer surface 151 has an outwardly convex shape, and the anterior boundary line at which the outer surface 151 meets the anterior-facing surface 1537 may be formed as a straight line that straightly connects the top anterior point 1511a and the lower anterior point 1511b. Particularly, since the anterior boundary line 1511 is a line that meets the anterior-facing surface 1537 perpendicular to the top surface 11, the anterior boundary line 1511 may also extend vertically to the top surface 11. This configuration can be seen in FIG. 9, which is a side view of the augment 1. As described above, the anterior boundary line 1511 is extends perpendicular to the top surface 11, which makes it possible to quickly, easily, and accurately evaluate the alignment state between the tibia 91 and the augment 1 with naked eyes when the alignment state between the tibia 91 and the augment 1 is checked using a X-ray photograph after the operation is completed. In this case, the curvature of the outer surface 151 continuously vary depending on the position to have a continuous distribution in order to ensure that the outer surface 151 formed as a curved surface and the perpendicularly and straightly extending anterior-boundary line 1511 are naturally connected to each other.

In addition, the posterior boundary line 1513, which is the line at which the outer surface 151 meets the rear surface 155, may also be formed as a straight line that connects the top posterior point 1513a and the bottom posterior point 1513b. In order to ensure that the posterior boundary line 1513 formed as a straight line as described above and the outer surface 151 forming a curved surface are naturally connected to each other, the curvature of the outer surface 151 may continuously change to have a continuous distribution.

Like the inner surface 153, the rear surface 155 may extend to be perpendicular to the top surface 11, and meets the outer surface 151 with reference to the posterior boundary line 1513. Since the rear surface 155 extends to be perpendicular to the top surface 11, it is possible to quickly, easily, and accurately check the alignment state when the alignment state is checked from the side using X-ray after implantation of the augment 1.

The coupling holes 17 are holes that that are recessed by a predetermined depth from the top surface 11 toward the bottom surface 13, and are located at points aligned with the coupling means accommodation holes 315 that penetrate the proximal surface 311 and distal surface 313 of the base plate 31, thereby accommodating coupling means (not illustrated). As described above, it is possible to quickly and easily determine the position of the augment 1 when positioning the augment 1 on the distal surface 313 of the base plate 31 while accommodating the coupling means. Further, it is possible to further reinforce coupling force after coupling, and thus to increase the life of the implant.

Next, the principle of coupling the augment 1 to the tibia element 3 according to the present disclosure and the process of implementing the augment 1 to a tibia 91 will be described in detail with reference to FIGS. 13 to 17.

Figure 14:
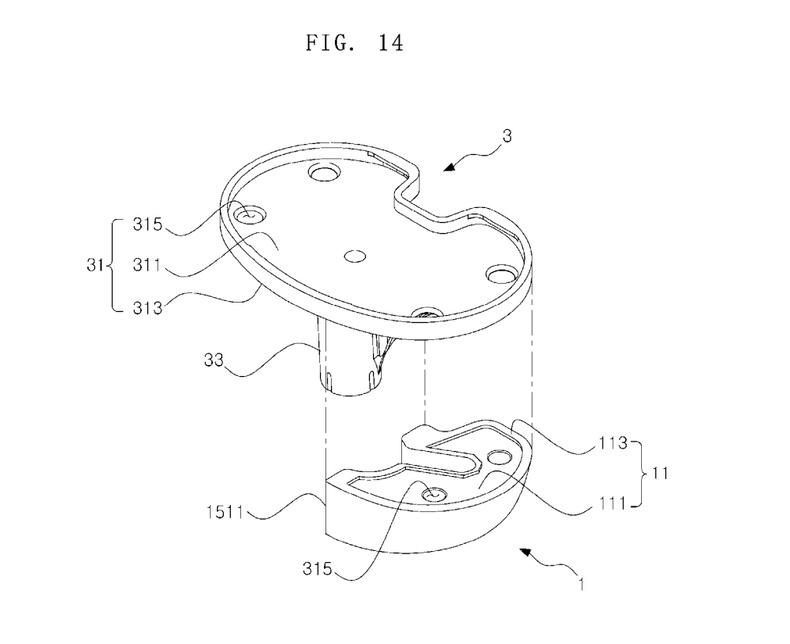
FIG. 14 is a perspective view illustrating a process in which the augment according to an embodiment of the present disclosure is coupled to a tibia element.

Referring to FIGS. 14 to 15, after applying adhesive or the like to the upper recessed surface 111 formed in the top surface 11 of the augment 1, the augment 1 is coupled to the distal surface 313, which is the bottom surface of the base plate 31 of the tibia element 3. In this case, when the wing 35 of the tibia element 3 is accommodated in the wing accommodation surface 1531, the stem 33 comes into contact with the first and second stem accommodation surfaces 1533 and 1535. In addition, coupling means (not illustrated) are introduced into the coupling holes 17 and the coupling means accommodation holes 315 to strengthen the coupling force between the augment 1 and the tibia element 3. In some cases, two augments 1 may be coupled to the opposite sides of the tibia element 3. At this time, the augments 1 at the opposite sides have symmetrical shapes. Since the augments 1 on the opposite sides are symmetrical to each other with respect to the stem 33, two types of augments 1 can be used for both of left and right knees. This symmetrical structure is also illustrated in FIG. 11.

Referring to FIG. 16, it can be seen that two augments 1 having different thicknesses are coupled to respective opposite sides of the tibia element 3. Depending on the state of the tibia 91 of the patient, the extent of cutting the proximal portion 911 may vary, and thus augments 1 having various thicknesses are required. As illustrated in FIG. 16, when the heights of the inner and outer cut surfaces 9111a and 9111b are different, two augments 1 having different thicknesses may be used.

Figure 17:
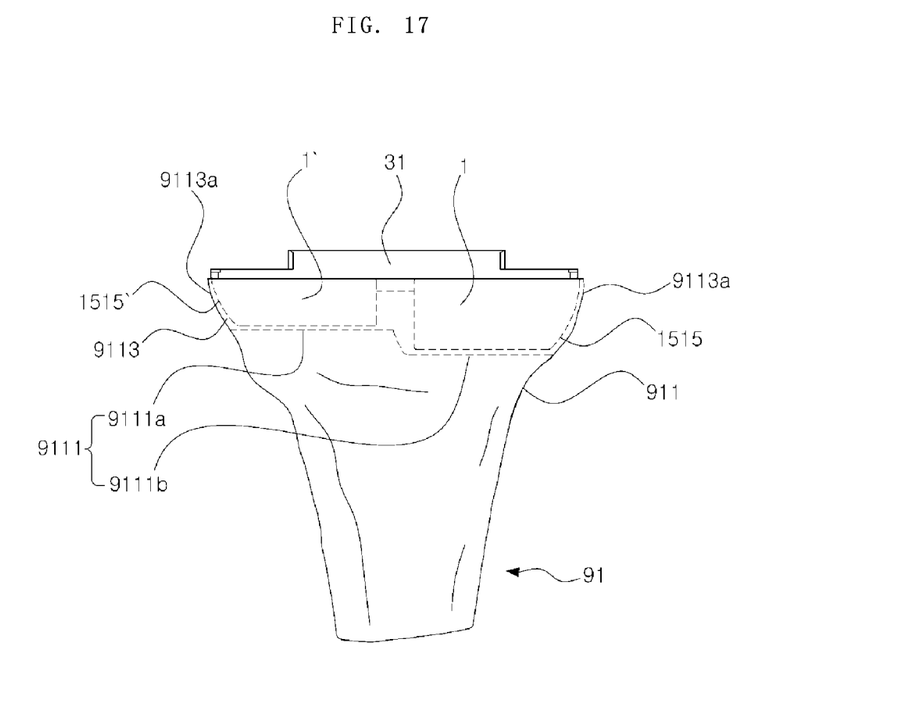
FIG. 17 is a front view illustrating the state in which the augment and the tibia element according to an embodiment of the present disclosure are coupled to a proximal portion of a tibia.

Referring to FIG. 17, the augment 1 according to the present disclosure forms a curved surface when the outer surface 151 thereof extends upward from the bottom, and thus the middle line 1515, which is observed when viewed from the front side, extends similarly to the external profile 9113a of the cut tibia portion 9113. When comparing this with the conventional augment illustrated in FIG. 3, the difference therebetween can be more clearly understood.

With this configuration, the augment 1 can be closer to the anatomical shape of the tibia 91, and can withstand a load by reinforcing lost bone as much as possible. As a result, since the distribution of the load, applied when the patient who recovered after completing the replacement of a knee joint walks or moves a heavy object, is formed similar to that in the case where the actual bone is present, it is possible to smoothly perform an exercise. In addition, it is possible to increase the lifespan of the implant by preventing force from concentrating to only one side of the implant.

The foregoing detailed description exemplifies the present disclosure. In addition, the foregoing description is intended to illustrate and explain embodiments of the present disclosure, and the present disclosure may be used in various other combinations, modifications, and environments. That is, it is possible to change or modify the present disclosure within the scope of the concept of the present disclosure disclosed in this specification, within the scope equivalent to the above-described contents, and/or within the scope of the skill or knowledge in the art. The embodiments described above are intended to illustrate the best mode for carrying out the technical idea of the present disclosure, and various modifications required for specific applications and uses of the present disclosure are also possible. Therefore, the detailed description of the present disclosure is not intended to limit the present disclosure to the disclosed embodiments. In addition, the appended claims should be interpreted as covering other embodiments as well.

What is claimed is:

1. A tibial baseplate augment having a size and shape corresponding to an anatomical structure of a lost proximal tibia, the augment including a top surface configured to come into contact with a distal surface of a tibial baseplate and a bottom surface configured to come into contact with a cut surface of the proximal tibia,
   wherein the bottom surface of the augment has a shape having a smaller area than the top surface so as to correspond to the anatomical structure of the lost proximal tibia,
   wherein an outer surface connecting the top and bottom surfaces of the augment is formed as a curved surface so as to correspond to the anatomical structure of the lost proximal tibia,
   wherein the outer surface of the augment is formed as a curved surface that is outwardly convex while extending from the top surface to the bottom surface and that is continuously inwardly inclined from the top surface toward the bottom surface,
   wherein a middle line at which one end surface cut to be perpendicular to the top surface meets the outer surface takes a form of a curved line convex to the outside of the augment with respect to a straight line connecting a top point at which the middle line meets the top surface and a bottom point at which the middle line meets the bottom surface,
   wherein an anterior boundary line at which an inner surface connecting the top and bottom surfaces of the augment and the outer surface meet on an anterior side extends to be perpendicular to the bottom surface,
   wherein the inner surface includes a wing accommodation surface configured to accommodate a wing of the tibial baseplate.

2. The augment of claim 1, further comprising:
   a rear surface connecting the outer surface and the inner surface on a posterior side, the rear surface extending to be perpendicular to the top surface.

3. The augment of claim 2, wherein the inner surface extends to be perpendicular to the top surface.

4. The augment of claim 1, wherein the top surface includes an upper recessed surface that is recessed downward by a predetermined depth in order to accommodate adhesive.

5. The augment of claim 1, wherein the bottom surface includes a lower recessed surface that is recessed upward by a predetermined depth in order to accommodate adhesive.

6. The augment of claim 1, wherein the augment includes a coupling hole recessed downward by a predetermined depth from a top surface of the tibial baseplate.

7. The augment of claim 1, wherein two augments are provided to be respectively coupled to opposite sides of the distal surface of the tibial baseplate, and the two augments are formed in symmetrical shapes with reference to a stem of the tibial baseplate, whereby the two augments can be used for both of left and right knees.

* * * * *